(12) United States Patent
Yamanaka

(10) Patent No.: US 10,786,909 B2
(45) Date of Patent: Sep. 29, 2020

(54) SWING MECHANISM AND GRIPPING TOOL

(71) Applicant: OLYMPUS CORPORATION, Tokyo (JP)

(72) Inventor: Noriaki Yamanaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 58 days.

(21) Appl. No.: 16/256,298

(22) Filed: Jan. 24, 2019

(65) Prior Publication Data

US 2019/0152069 A1 May 23, 2019

Related U.S. Application Data

(63) Continuation of application No. PCT/JP2016/081177, filed on Oct. 20, 2016.

(51) Int. Cl.
 *B25J 15/08* (2006.01)
 *B25J 17/02* (2006.01)
 (Continued)

(52) U.S. Cl.
 CPC ............... *B25J 15/08* (2013.01); *A61B 17/29* (2013.01); *A61B 34/30* (2016.02); *A61B 34/71* (2016.02);
 (Continued)

(58) Field of Classification Search
 CPC . B25J 9/104; B25J 9/1045; B25J 15/08; B25J 15/0233; B25J 17/00; B25J 17/0241;
 (Continued)

(56) References Cited

U.S. PATENT DOCUMENTS 3,866,966 A * 2/1975 Skinner, II .............. A61F 2/588
 294/106
4,986,723 A * 1/1991 Maeda ........................ B25J 9/06
 294/111
(Continued)

FOREIGN PATENT DOCUMENTS

EP 1 854 418 A1 11/2007
EP 2 415 418 A1 2/2012
(Continued)

OTHER PUBLICATIONS

International Search Report dated Jan. 10, 2017 received in PCT/JP2016/081177.

*Primary Examiner* — Dean J Kramer
(74) *Attorney, Agent, or Firm* — Scully, Scott, Murphy & Presser, P.C.

(57) ABSTRACT

A swing mechanism according to the present invention includes: a first swing member that swings about a first swing shaft; a second swing member that is provided in the first swing member and that swings about a second swing shaft; a traction pulley that is supported by the second swing member and that rotates about a rotational shaft; a fixed pulley that rotates about the second swing shaft; and a wire that is looped around the fixed pulley and the traction pulley. On both sides of the traction pulley, tensions are generated in the same directions by a traction force applied to the other end of the wire. The traction pulley is disposed at a position at which the tensions in the wire acting on the rotational shaft brings about a moment for causing the second swing member to swing.

5 Claims, 11 Drawing Sheets

(51) Int. Cl.
*A61B 17/29* (2006.01)
*A61B 34/30* (2016.01)
*B25J 17/00* (2006.01)
*A61B 34/00* (2016.01)

(52) U.S. Cl.
CPC ........... *B25J 17/00* (2013.01); *B25J 17/0241* (2013.01); *A61B 2017/2927* (2013.01)

(58) Field of Classification Search
CPC .................... B25J 17/025; A61B 17/29; A61B 2017/2927; A61B 2017/2929; A61B 2017/2932; A61B 2017/2941; A61B 34/71; A61B 2034/715
USPC ........................................................ 294/111
See application file for complete search history.

(56) References Cited

U.S. PATENT DOCUMENTS

| | | |
|---|---|---|
| 7,316,681 B2 | 1/2008 | Madhani et al. |
| 8,540,748 B2 * | 9/2013 | Murphy ................. A61B 34/71 606/205 |
| 2003/0208186 A1 * | 11/2003 | Moreyra ................ A61B 34/30 606/1 |
| 2004/0199147 A1 * | 10/2004 | Nishizawa ............. A61B 34/71 606/1 |
| 2007/0288044 A1 | 12/2007 | Jinno et al. |
| 2010/0198253 A1 | 8/2010 | Jinno et al. |
| 2013/0304084 A1 | 11/2013 | Beira et al. |
| 2015/0025549 A1 | 1/2015 | Kilroy et al. |
| 2015/0038981 A1 | 2/2015 | Kilroy et al. |
| 2015/0038982 A1 | 2/2015 | Kilroy et al. |
| 2015/0150635 A1 | 6/2015 | Kilroy et al. |
| 2015/0157410 A1 | 6/2015 | Kilroy et al. |
| 2015/0209965 A1 | 6/2015 | Low et al. |
| 2015/0366573 A1 * | 12/2015 | Hahnle ............ A61B 17/00234 606/205 |
| 2016/0316996 A1 | 11/2016 | Nakayama et al. |
| 2016/0338788 A1 * | 11/2016 | Hares ..................... A61B 34/30 |
| 2018/0050456 A1 | 2/2018 | Yamanaka |

FOREIGN PATENT DOCUMENTS

| | | |
|---|---|---|
| EP | 3 095 375 A1 | 11/2016 |
| JP | 2007-301692 A | 11/2007 |
| JP | 2010-227331 A | 10/2010 |
| JP | 2015-131015 A | 7/2015 |
| JP | 2016-518160 A | 6/2016 |
| WO | 2010/090292 A2 | 8/2010 |
| WO | 2016/194067 A1 | 12/2016 |
| WO | 2016/194777 A1 | 12/2016 |

* cited by examiner

US 10,786,909 B2

SWING MECHANISM AND GRIPPING TOOL

CROSS-REFERENCE TO RELATED APPLICATIONS

This is a continuation of International Application PCT/JP2016/081177, with an international filing date of Oct. 20, 2016, which is hereby incorporated by reference herein in its entirety.

TECHNICAL FIELD

The present invention relates to a swing mechanism and a gripping tool.

BACKGROUND ART

In gripping mechanisms for gripping an object, such as living tissue, by means of a pair of gripping pieces coupled so as to be capable of swinging, there is a known gripping mechanism using a toggle mechanism (for example, see Japanese Unexamined Patent Application, Publication No. 2007-301692). The toggle mechanism is provided with a pair of links coupled so as to be capable of swinging about the same swing shaft as the pair of gripping pieces, and an opening operation of the pair of links is converted into a closing operation of the pair of gripping pieces. In this structure, the gripping force of the pair of gripping pieces can be increased in accordance with the length of the pair of links.

SUMMARY OF INVENTION

According to a first aspect, the present invention provides a swing mechanism including: a base member; a first swing member that is supported so as to swing about a first swing shaft with respect to the base member; a second swing member that is provided in the first swing member, the second swing member is supported so as to swing about a second swing shaft disposed with a gap interposed in a direction perpendicular to the first swing shaft; a traction pulley that is supported by the second swing member so as to rotate about a rotational shaft disposed with a gap interposed in a direction perpendicular to the second swing shaft; a fixed pulley that is supported so as to rotate about the first swing shaft; and a wire that is looped around the fixed pulley and the traction pulley, one end of the wire is fixed to the base member, the first swing member, or the second swing member, and in which tensions in substantially the same directions are generated on both sides of the traction pulley with the rotational shaft therebetween, by a traction force applied to the other end of the wire, wherein the traction pulley is disposed at a position at which the resultant force of the tensions in the wire acting on the rotational shaft brings about a moment for causing the second swivel member to swivel.

DESCRIPTION OF EMBODIMENTS

A swing mechanism 3 and a gripping tool 1 according to one embodiment of the present invention will be described below with reference to the drawings.

Figure 1:
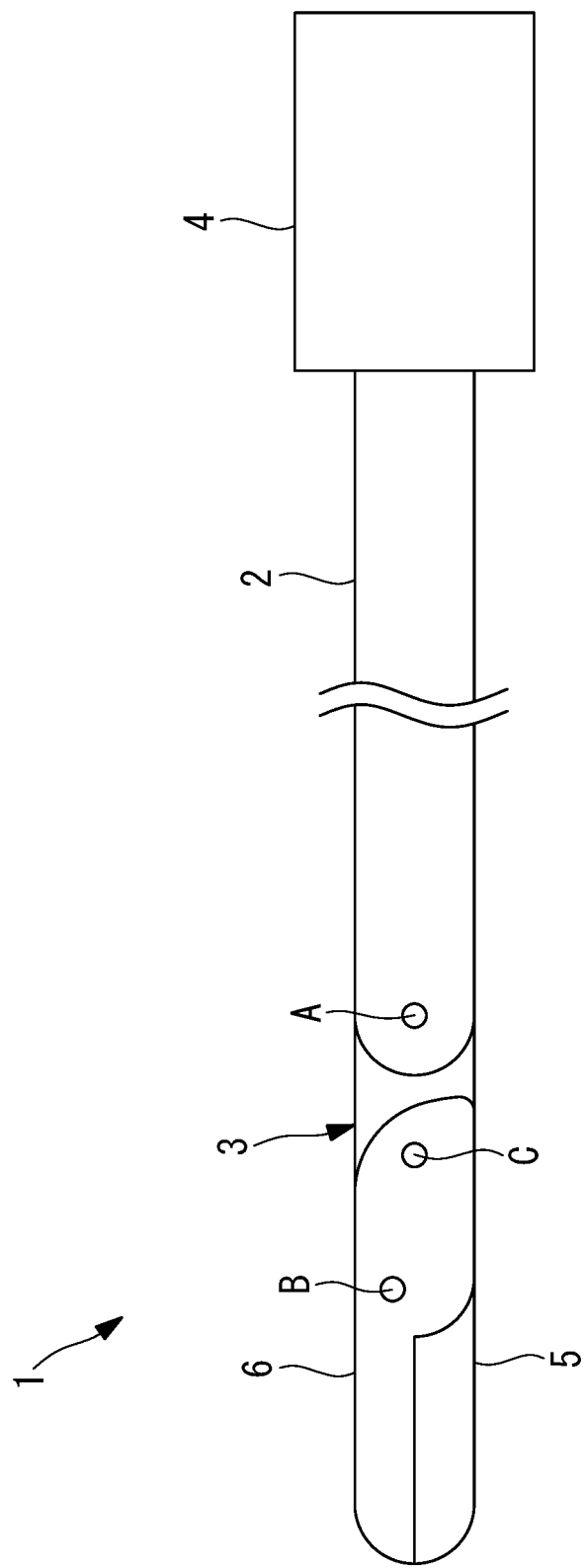
FIG. 1 is a view showing the overall configuration of a gripping tool according to one embodiment of the present invention.

The gripping tool 1 of this embodiment is a medical device having a function of gripping living tissue, in the same manner as grasping forceps. As shown in FIG. 1, the gripping tool 1 is provided with: the swing mechanism 3 according to this embodiment, having an elongated body part (base member) 2 that can be inserted into the human body; and a drive unit 4 that is connected to a proximal end of the body part 2.

Figure 2:
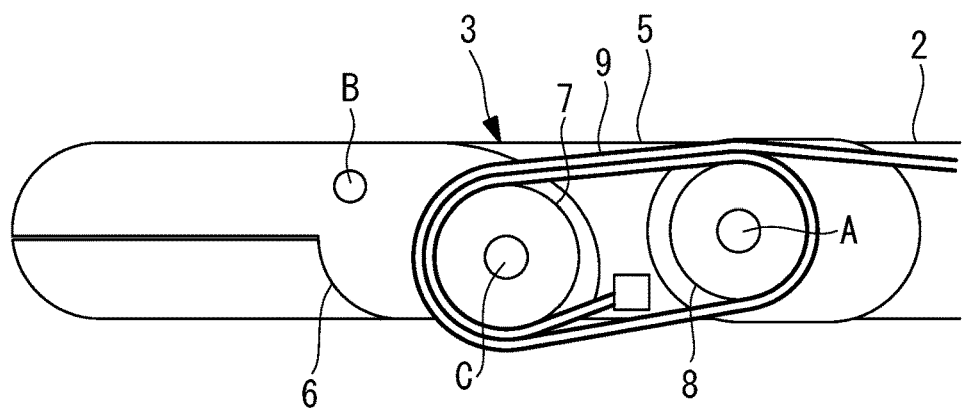
FIG. 2 is a partially cut-out side view showing a swivel mechanism according to the one embodiment of the present invention, which is provided in the gripping tool shown in FIG. 1.

As shown in FIG. 2, the swing mechanism 3 of this embodiment is provided with: the body part 2; a first gripping piece (first swing member) 5 that is attached so as to be capable of swinging about a first swing shaft A perpendicular to the longitudinal axis of the body part 2; a second gripping piece (second swing member) 6 that is provided on the first gripping piece 5 and that is attached so as to be capable of swinging about a second swing shaft B parallel to the first swing shaft A; a traction pulley 7 that is supported by the second gripping piece 6 so as to be capable of rotating about a rotational shaft C; a fixed pulley 8 that is supported so as to be capable of rotating about the first swing shaft A; and a wire 9 that is looped around the traction pulley 7 and the fixed pulley 8. The first gripping piece 5 and the second gripping piece 6 constitute a pair of gripping parts.

In the example shown in FIG. 2, one end of the wire 9 is fixed to the first gripping piece 5, and the other end of the wire 9 extends toward the proximal end of the body part 2 and is connected to the drive unit 4.

The wire 9 extends from the one end, which is fixed to the first gripping piece 5, toward the traction pulley 7, is looped around the traction pulley 7, is then looped around the fixed pulley 8, is again looped around the traction pulley 7, and is guided to the drive unit 4, which is located at the proximal end of the body part 2.

The traction pulley 7 and the fixed pulley 8 have substantially the same diameters, so that sections of the wire 9 disposed therebetween extend substantially in parallel in the direction of the gap between the rotational shaft C of the traction pulley 7 and the first swing shaft A of the fixed pulley 8. Two sections of the wire 9 are looped around the traction pulley 7, and extend on each of both sides of the traction pulley 7 with the rotational shaft C therebetween.

The drive unit 4 has a motor (not shown) to which the other end of the wire 9 is connected and pulls the wire 9 toward the proximal end through actuation of the motor, thus generating tensions in the wire 9.

Figure 3:
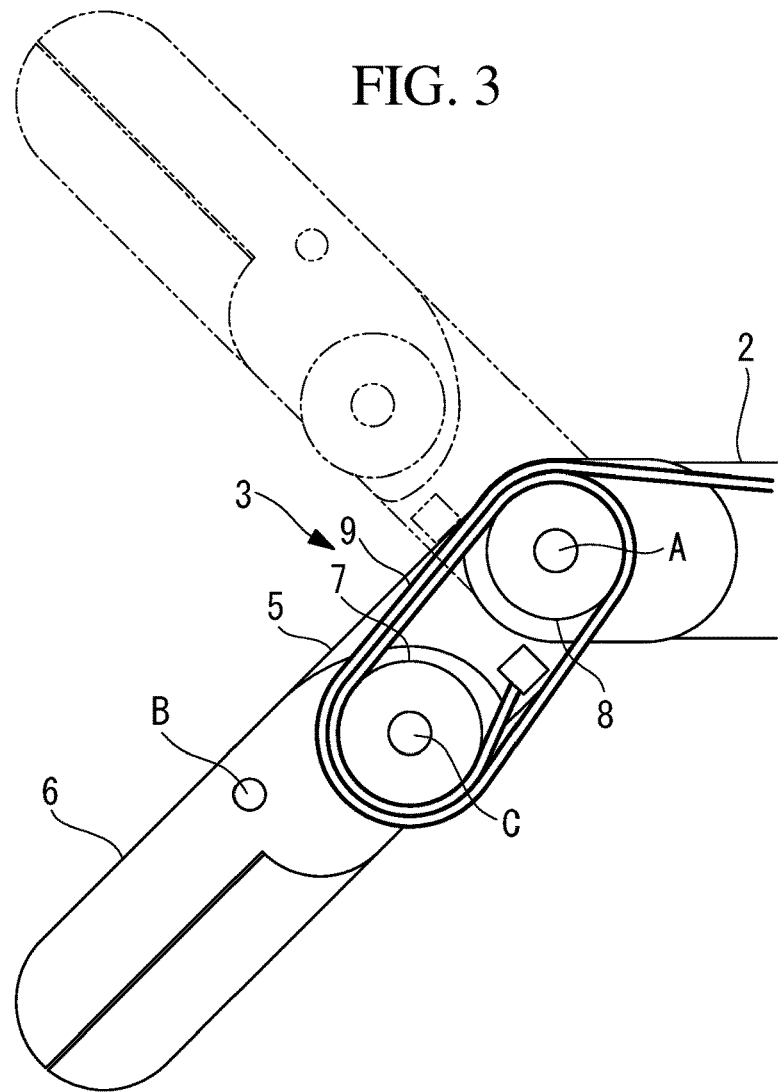
FIG. 3 is a side view showing a state in which two gripping pieces of the gripping tool shown in FIG. 1 are made to swing with respect to a body part.

The first gripping piece 5 is made to swing about the first swing shaft A with respect to the body part 2 by means of a drive mechanism (not shown), as shown in FIG. 3, thereby making it possible to integrally change the directions of the first gripping piece 5 and the second gripping piece 6 with respect to the body part 2.

Distal end sections of the first gripping piece 5 and the second gripping piece 6 can be mutually opened and closed by swinging the second gripping piece 6 about the rotational shaft B with respect to the first gripping piece 5. Accordingly, in the example shown in FIG. 4, it is possible to grip living tissue or the like, which is a gripping target, by means of the pair of gripping parts, which are constituted by the distal ends of the first gripping piece 5 and the second gripping piece 6.

Figure 4:
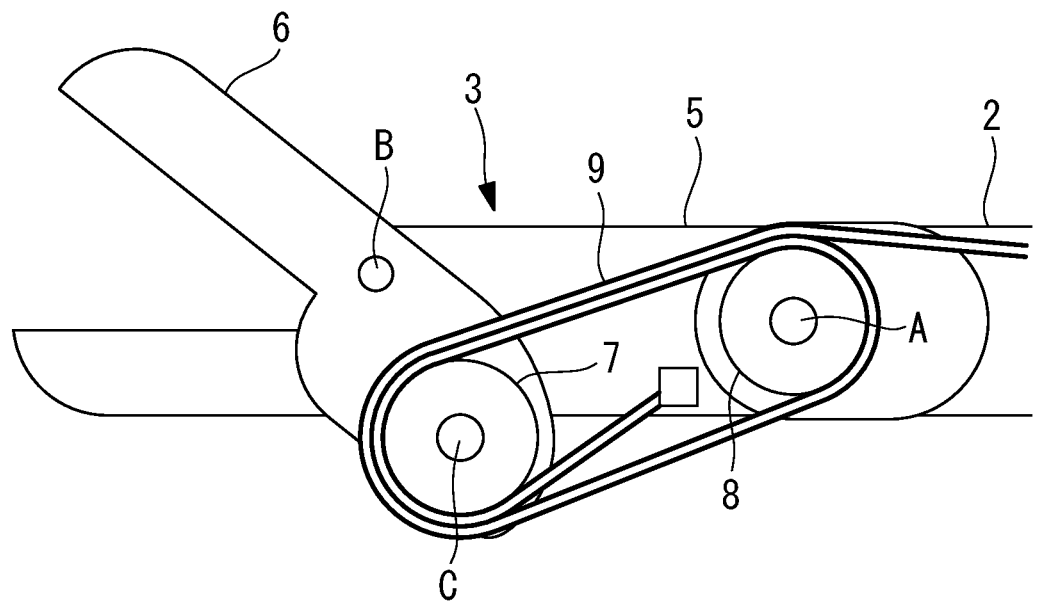
FIG. 4 is a partially cut-out side view showing a state in which a second gripping piece is made to swing with respect to a first gripping piece by means of the swing mechanism shown in FIG. 2.

In a state in which the first gripping piece 5 and the second gripping piece 6 are closed, as shown in FIG. 2, and in a state in which the first gripping piece 5 and the second gripping piece 6 are opened, as shown in FIG. 4, the rotational shaft C, which supports the traction pulley 7 in a rotatable manner, is disposed such that a straight line connecting the rotational shaft C and the first swing shaft A is disposed so as to be away from the second swing shaft B in any one direction.

In this embodiment, as described later, the rotational shaft C is disposed at such a position that, due to tensions generated in the wire 9 by applying a traction force to the wire 9, the traction force acting on the rotational shaft C of the traction pulley 7 brings about a moment in the direction in which the second gripping piece 6 is closed with respect to the first gripping piece 5.

The operation of the thus-configured swing mechanism 3 and gripping tool 1 of this embodiment will now be described.

According to the swing mechanism 3 of this embodiment, when the wire 9 is pulled toward the proximal end through actuation of the drive unit 4, tensions are generated in the wire 9. Because substantially the same magnitudes of tensions act on the wire 9, which is looped around the traction pulley 7, and the total four sections of which extend on both sides, i.e., two sections on each side, of the traction pulley 7 with the rotational shaft C therebetween, the resultant force of the tensions generated in the four sections of the wire 9 acts on the rotational shaft C. Specifically, because the resultant force substantially four times the traction force applied to the proximal end of the wire 9 acts on the rotational shaft C, there is an advantage in that the second gripping piece 6 can be made to swing with respect to the first gripping piece 5 with a small traction force.

The swing angle of the second gripping piece 6 with respect to the first gripping piece 5 is not limited structurally, a large swing angle of the second gripping piece 6 with respect to the body part 2 can be ensured.

In this case, because the fixed pulley 8 is provided on the first swing shaft A so as to be rotatable, there is an advantage in that, compared with a case in which the fixed pulley 8 is provided between the second swing shaft B and a joint that causes the first gripping piece 5 to swing with respect to the body part 2, it is possible to reduce the length of a rigid part disposed closer to the distal end than the joint is and to improve the operability in a narrow place.

In this embodiment, although the wire 9 is looped between the fixed pulley 8 and the traction pulley 7 twice, instead of this, the wire 9 may be looped between the fixed pulley 8 and the traction pulley 7 three or more times. Accordingly, even when the wire 9 is pulled by the same traction force, the force for closing the second gripping piece 6 with respect to the first gripping piece 5 can be increased.

In this embodiment, although the position of the traction pulley 7 is set such that traction of the wire 9 brings about a moment for causing the second gripping piece 6 to swing in the closing direction with respect to the first gripping piece 5, instead of this, the position of the traction pulley 7 may be set such that traction of the wire 9 brings about a moment for causing the second gripping piece 6 to swing in the opening direction with respect to the first gripping piece 5.

In this embodiment, although the distal end of the wire 9 is fixed to the first gripping piece 5, instead of this, the distal end of the wire 9 may be fixed to the second gripping piece 6 or to the body part 2.

Figure 5:
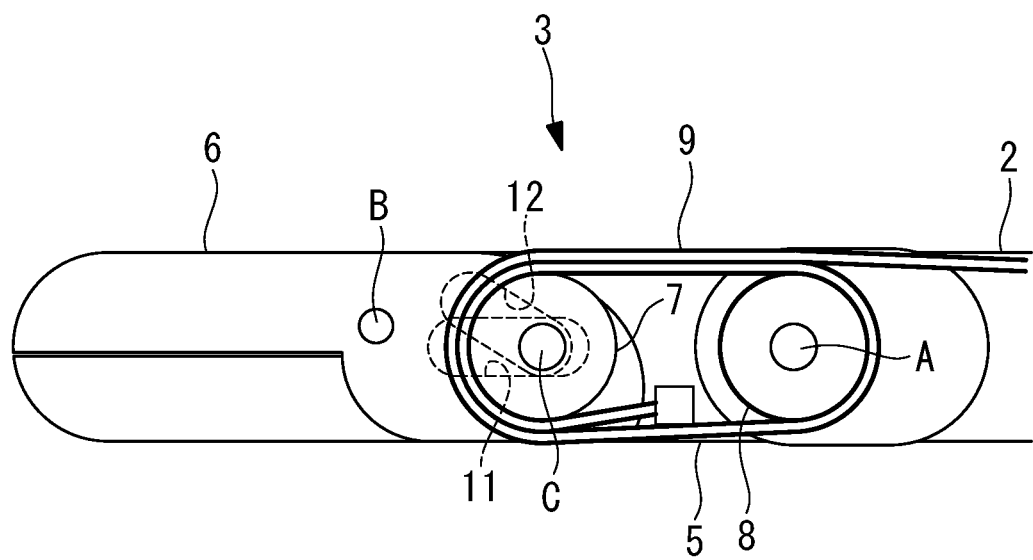
FIG. 5 is a partially cut-out side view showing a first modification of the swing mechanism shown in FIG. 2.
Figure 6:
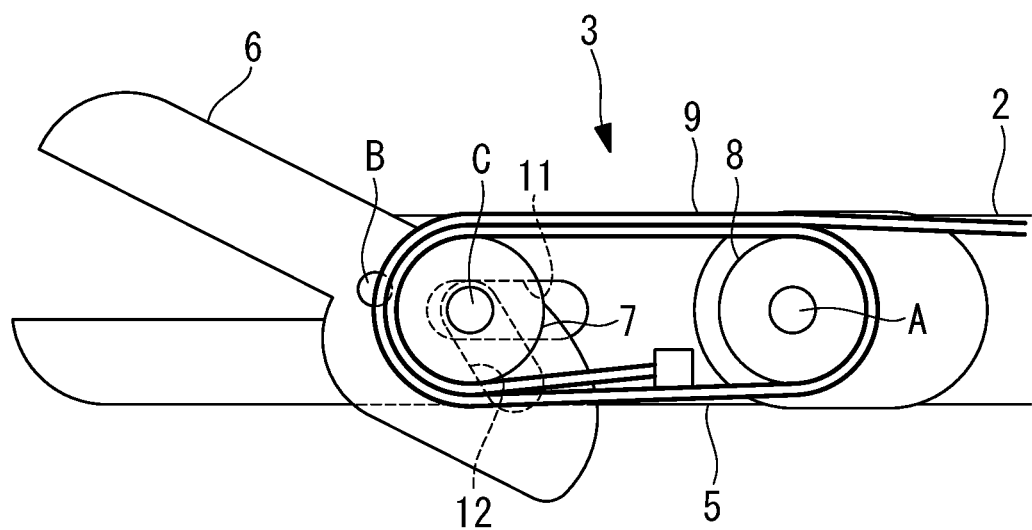
FIG. 6 is a partially cut-out side view showing a state in which the second gripping piece is made to swing with respect to the first gripping piece by means of the swing mechanism shown in FIG. 5.

In this embodiment, although the traction pulley 7 is attached so as to be capable of rotating about the rotational shaft C fixed to the second gripping piece 6, instead of this, as shown in FIGS. 5 and 6, the rotational shaft C of the traction pulley 7 may be accommodated so as to be capable of moving in the longitudinal directions of a first slit 11 and a second slit 12 that are provided in the first gripping piece 5 and the second gripping piece 6, respectively.

In this case, the first slit 11 is formed in the first gripping piece 5 along a straight line connecting the first swing shaft A and the second swing shaft B, and the second slit 12, which is inclined with respect to the first slit 11, is formed in the second gripping piece 6.

When a traction force is applied to the wire 9, the rotational shaft C is guided by means of the first slit 11, the traction pulley 7 is moved in such a direction as to approach the fixed pulley 8, and the second gripping piece 6 is moved so as to keep the rotational shaft C in an accommodated state in the second slit 12, thereby causing the second gripping piece 6 to swing about the second swing shaft B with respect to the first gripping piece 5.

Figure 7:
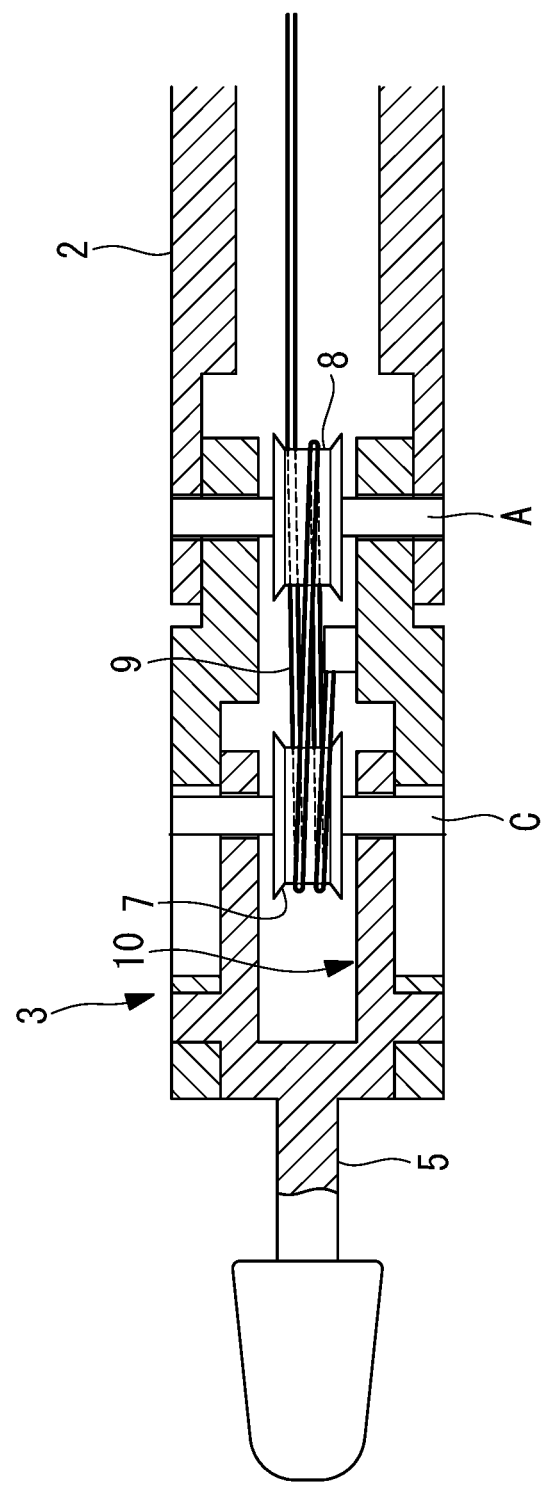
FIG. 7 is a longitudinal sectional view of the swing mechanism shown in FIG. 5, viewed from a direction perpendicular to a swing shaft.

If such a configuration is used, as shown in FIG. 7, it is preferred that the body part 2, the first gripping piece 5, and the second gripping piece 6 be formed to be hollow, and the fixed pulley 8 and the traction pulley 7 be disposed in a hollow portion 10. A traction force of the wire 9 can be applied to the centers of the first gripping piece 5 and the second gripping piece 6, thus making it possible to prevent the occurrence of a torsional moment. The pulleys, which have large outer diameters, are disposed at the center in the radial direction, thereby making it possible to reduce the size of the outer diameter of the gripping tool 1.

Figure 8:
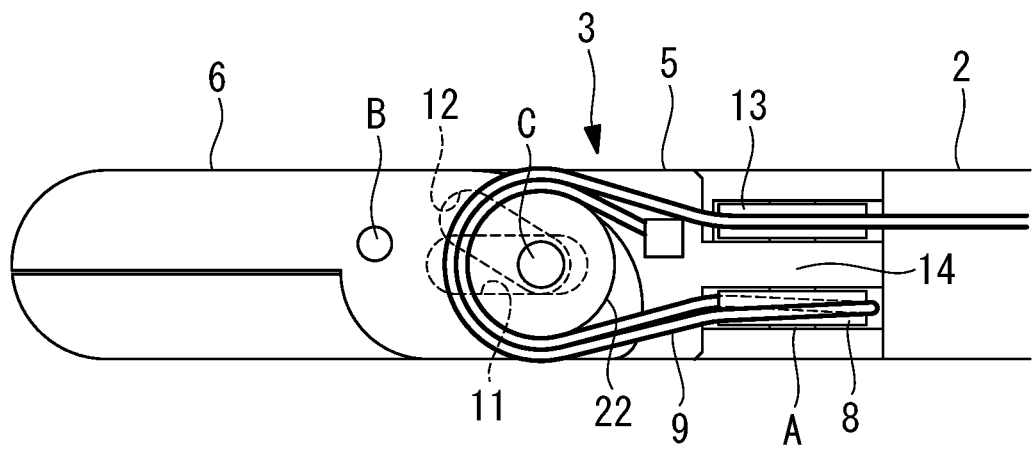
FIG. 8 is a partially cut-out side view showing a second modification of the swing mechanism shown in FIG. 2.
Figure 9:
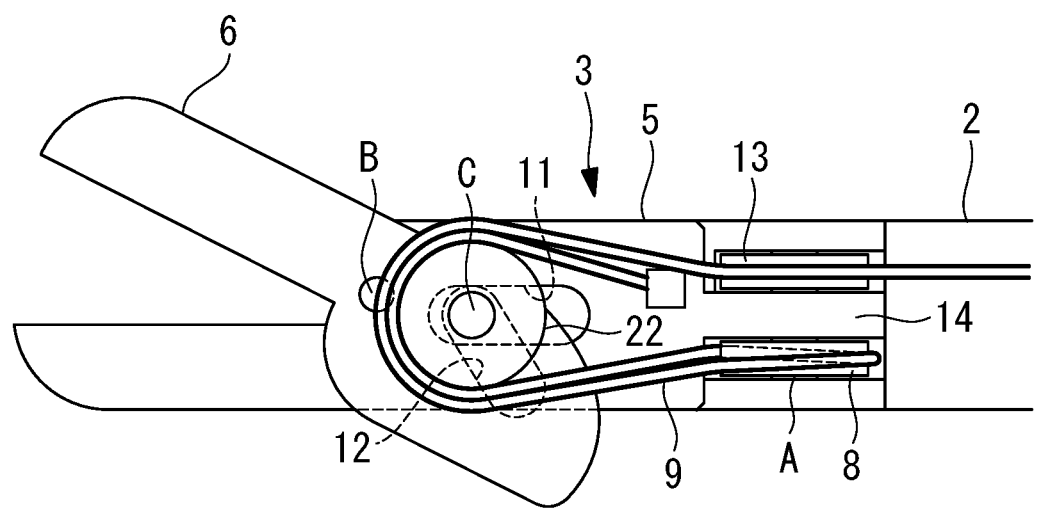
FIG. 9 is a partially cut-out side view showing a state in which the second gripping piece is made to swing with respect to the first gripping piece by means of the swing mechanism shown in FIG. 8.

Furthermore, although this embodiment shows an example case in which the first swing shaft A and the second swing shaft B are disposed substantially in parallel, instead of this, as shown in FIGS. 8 and 9, the first swing shaft A and the second swing shaft B may be disposed on a skew line. Specifically, the second swing shaft B, which is disposed at a position closer to the distal end than the first swing shaft A is with a gap therebetween, is disposed such that a plane including the first swing shaft A and the longitudinal axis of the first gripping piece 5 and a plane including the second swing shaft B and the longitudinal axis of the first gripping piece 5 are perpendicular to each other.

Accordingly, the swing direction of the first gripping piece 5 about the first swing shaft A with respect to the body part 2 and the swing direction of the second gripping piece 6 about the second swing shaft B with respect to the first gripping piece 5 are perpendicular to each other.

In a case in which the first swing shaft A and the second swing shaft B are in parallel, the swing of the first gripping piece 5 with respect to the body part 2 and the swing of the second gripping piece 6 with respect to the first gripping piece 5 have a redundant relationship; however, when the first swing shaft A and the second swing shaft B are made perpendicular to each other, there is an advantage in that the range of motion is extended, thus making it possible to more easily perform an action for causing the rigid part at the distal end of the gripping tool 1 to approach a desired position, in a narrow region.

Figure 10:
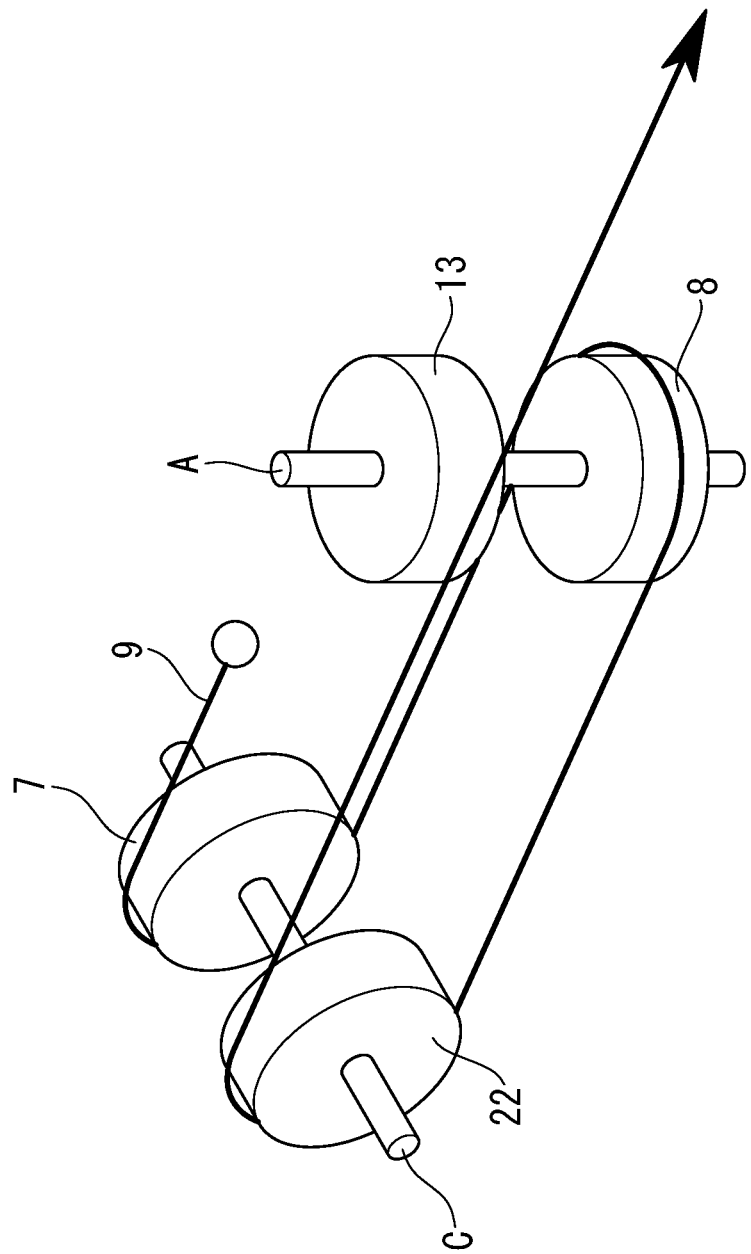
FIG. 10 is a perspective view showing an example arrangement of traction pulleys and fixed pulleys in the swing mechanism shown in FIG. 8.

Furthermore, in this case, as shown in FIG. 10, it is preferred that two traction pulleys 7 and 22 be provided in the longitudinal direction of the rotational shaft C with a gap therebetween, two fixed pulleys 8 and 13 be provided in the longitudinal direction of the first swing shaft A with a gap therebetween, and the wire 9 be looped around the same side surfaces of the two traction pulleys 7 and 22, between the two traction pulleys 7 and 22 and the fixed pulley 8, thus causing the two traction pulleys 7 and 22 to rotate in the opposite directions. The fixed pulley 13 in the figure functions as a guide pulley for guiding the wire 9.

By doing so, there is an advantage in that it is possible to perform routing such that sections of the wire 9 are not brought into close contact and to prevent entanglement and friction between sections of the wire 9.

Furthermore, in the example shown in FIGS. 8 and 9, a connection part 14 for the body part 2 and the first gripping piece 5 is disposed by using the space between the two fixed pulleys 8 and 13, which are disposed in accordance with the outer diameter of the traction pulley 7, thus making it possible to achieve a reduction in diameter by efficiently using the space.

Figure 11:
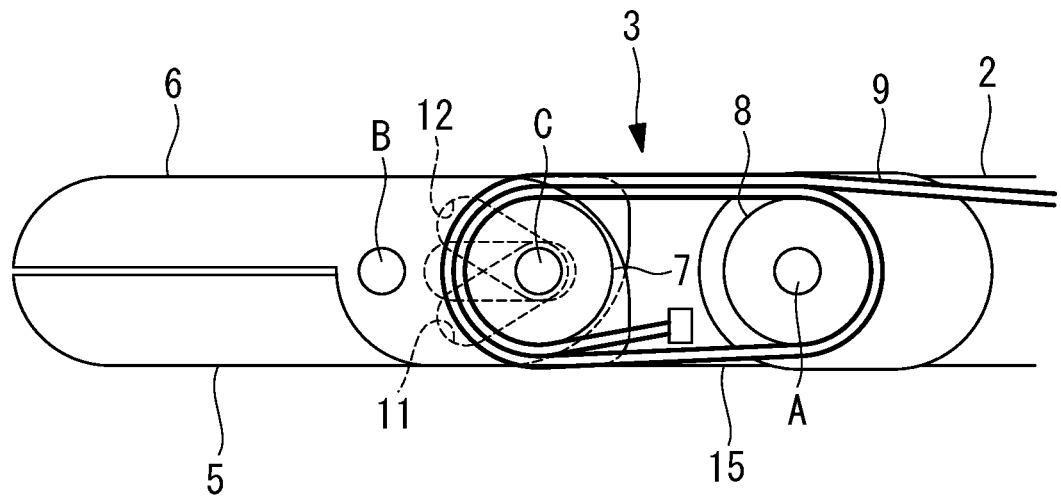
FIG. 11 is a partially cut-out side view showing a third modification of the swing mechanism shown in FIG. 2.
Figure 12:
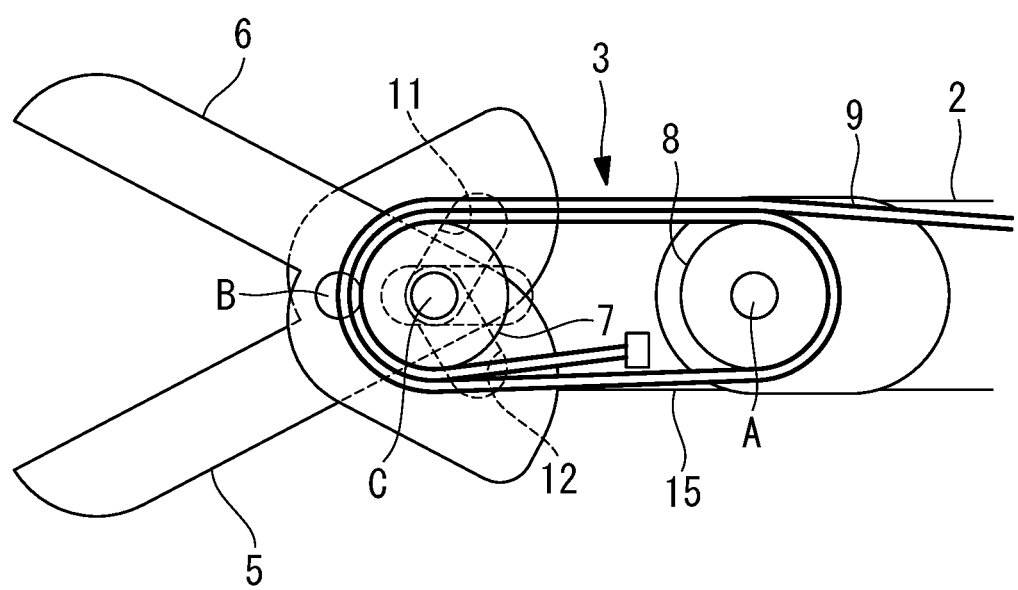
FIG. 12 is a partially cut-out side view showing a state in which the first gripping piece and the second gripping piece are both made to swing by means of the swing mechanism shown in FIG. 11.

Furthermore, in this embodiment, although a description has been given of an example way in which the second gripping piece 6 is made to swing with respect to the first gripping piece 5, instead of this, as shown in FIGS. 11 and 12, it is also possible to adopt a mechanism in which the first gripping piece 5 and the second gripping piece 6 both swing with respect to a first swing member 15 that is coupled to the body part 2 so as to be capable of swinging. By doing so, there is an advantage in that a large opening angle of the two gripping pieces 5 and 6 can be ensured.

In the above-described embodiment, although a description has been given of a case in which the swing mechanism 3 of this embodiment is used in the gripping tool 1, the present invention is not limited to this case and can also be applied to a joint mechanism that has two joint parts.

Figure 13:
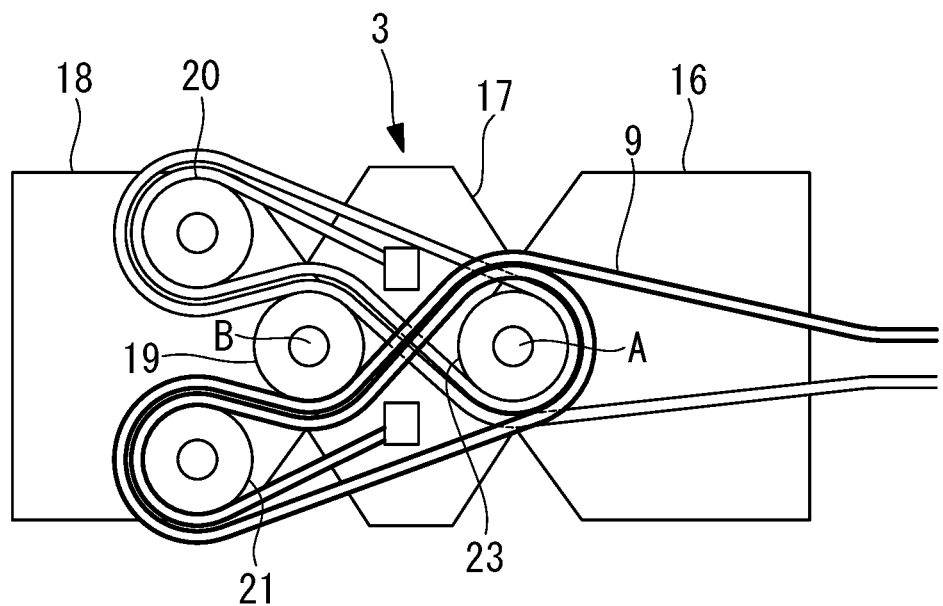
FIG. 13 is a partially cut-out side view showing a fourth modification of the swing mechanism shown in FIG. 2.
Figure 14:
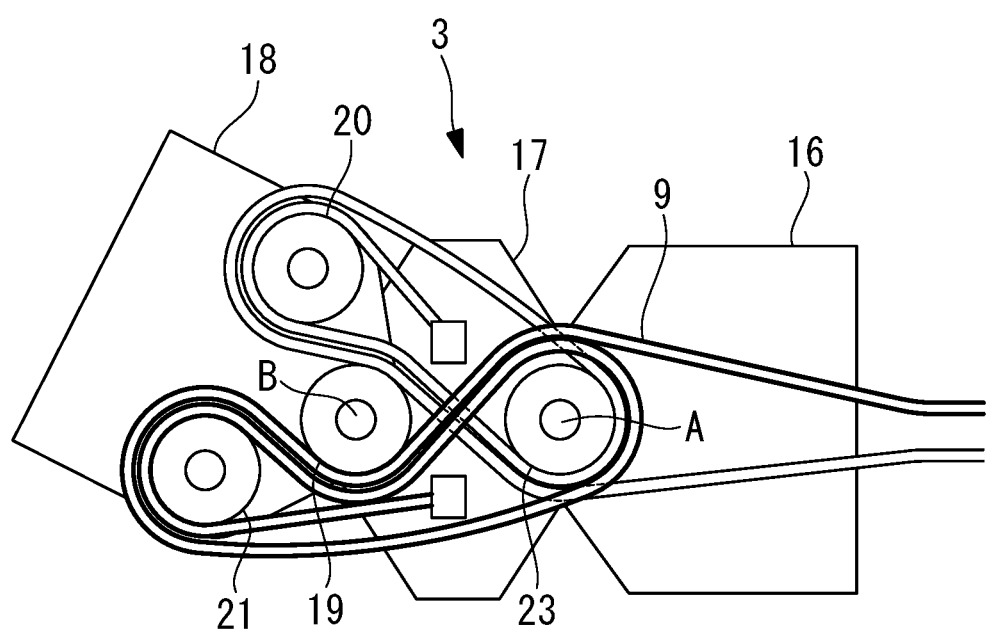
FIG. 14 is a partially cut-out side view showing a state in which joints are made to swing by means of the swing mechanism shown in FIG. 13.

For example, as shown in FIGS. 13 and 14, the swing mechanism 3 according to a modification is the same as that of the above-described embodiment in that a first swing member 17 that is attached so as to be capable of swinging about the first swing shaft A with respect to a base member 16 and a second swing member 18 that is attached so as to be capable of swinging about the second swing shaft B with respect to the first swing member 17 are provided, and wires 9, one end of each of which is fixed to the first swing member 17, are looped, more than two times, between two traction pulleys 20 and 21 and a fixed pulley 23 that is attached around the first swing shaft A, via a fixed pulley 19 attached to the second swing member 18 and are guided toward the proximal end. The fixed pulley 19 in the figure functions as a guide pulley for guiding the wires 9.

In the example shown in FIGS. 13 and 14, the first swing shaft A and the second swing shaft B are in parallel.

In the figure, the traction pulleys 20 and 21 are provided for the respective swing directions of the second swing member 18 with respect to the first swing member 17, so that the second swing member 18 can be made to swing in both directions with respect to the first swing member 17 by pulling the proximal ends of corresponding ones of the wires 9.

Figure 15:
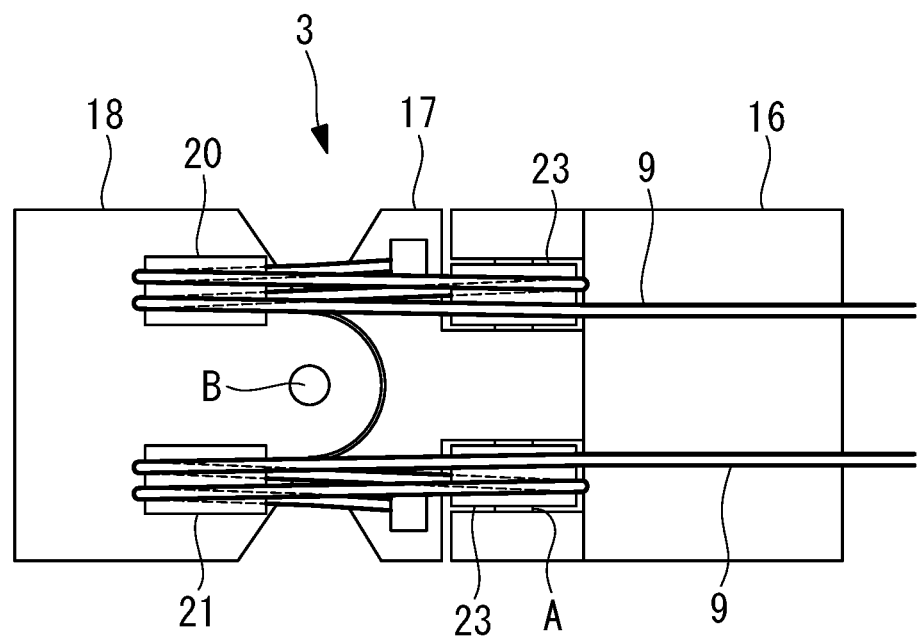
FIG. 15 is a partially cut-out side view showing a fifth modification of the swing mechanism shown in FIG. 2.
Figure 16:
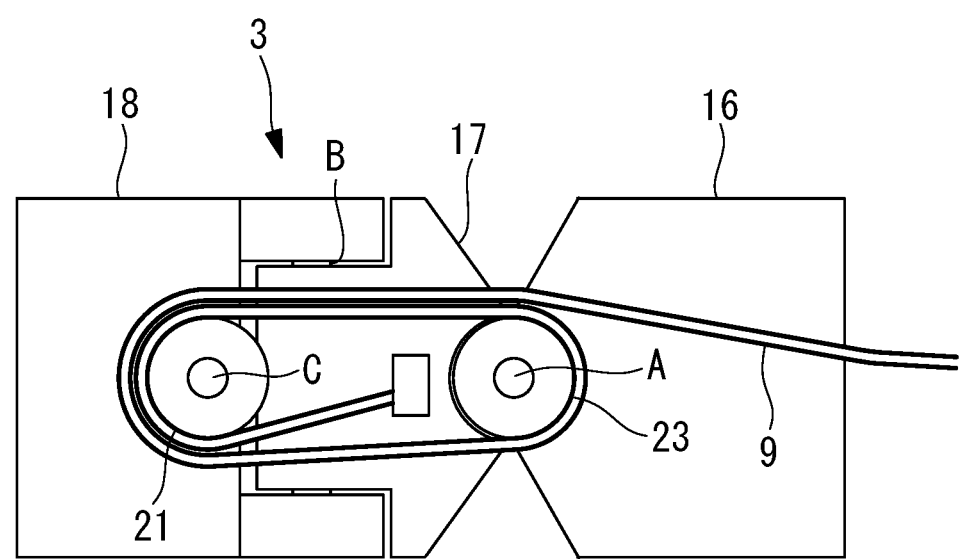
FIG. 16 is a side view of the swing mechanism shown in FIG. 15, viewed from a direction perpendicular to a second swing shaft.

As shown in FIGS. 15 and 16, even when the first swing shaft A and the second swing shaft B are disposed on a skew line, the same configuration can be used. In these figures, the rotational shaft C of the traction pulleys 20 and 21 and the first swing shaft A of the fixed pulleys 23 are disposed in parallel.

Figure 17:
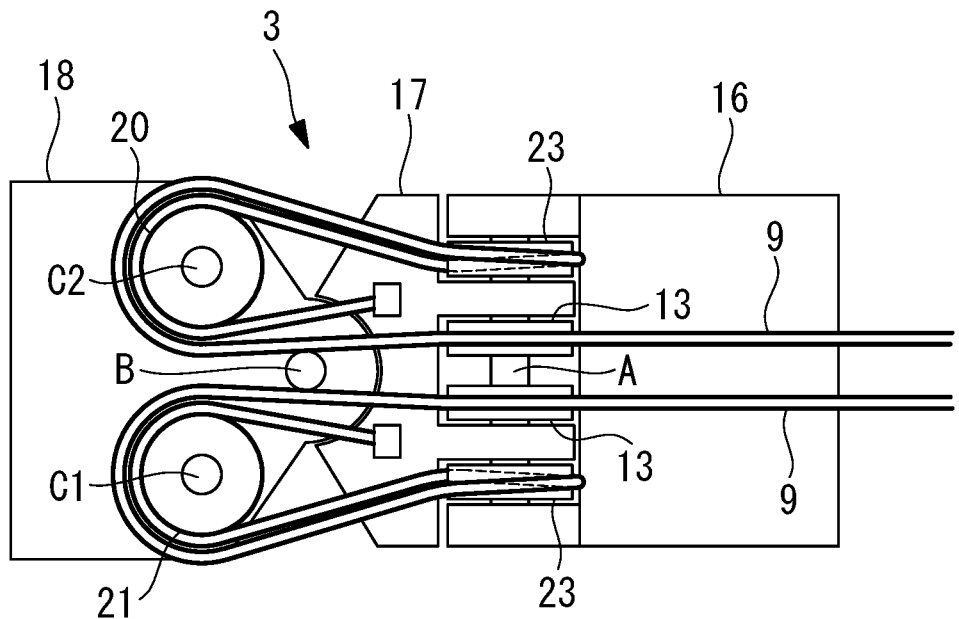
FIG. 17 is a partially cut-out side view showing a sixth modification of the swing mechanism shown in FIG. 2.
Figure 18:
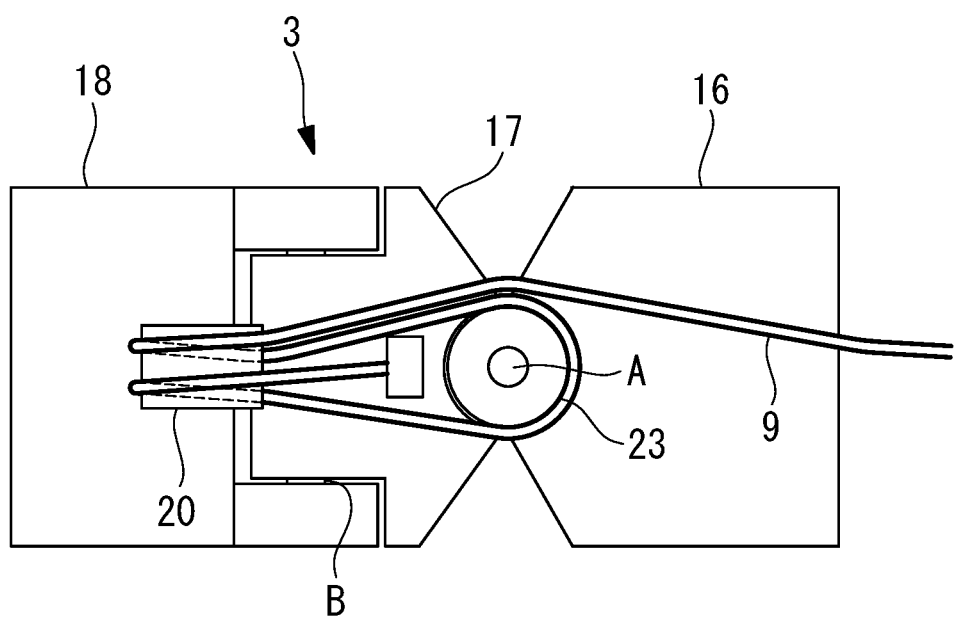
FIG. 18 is a side view of the swing mechanism shown in FIG. 17, viewed from a direction perpendicular to the second swing shaft.

Instead of this, as shown in FIGS. 17 and 18, rotational shafts C1 and C2 of the traction pulleys 20 and 21 and the first swing shaft A of the fixed pulleys 23 can be disposed on a skew line.

As a result, the following aspect is read from the above described embodiment of the present invention.

According to a first aspect, the present invention provides a swing mechanism including: a base member; a first swing member that is supported so as to swing about a first swing shaft with respect to the base member; a second swing member that is provided in the first swing member, the second swing member is supported so as to swing about a second swing shaft disposed with a gap interposed in a direction perpendicular to the first swing shaft; a traction pulley that is supported by the second swing member so as to rotate about a rotational shaft disposed with a gap interposed in a direction perpendicular to the second swing shaft; a fixed pulley that is supported so as to rotate about the first swing shaft; and a wire that is looped around the fixed pulley and the traction pulley, one end of the wire is fixed to the base member, the first swing member, or the second swing member, and in which tensions in substantially the same directions are generated on both sides of the traction pulley with the rotational shaft therebetween, by a traction force applied to the other end of the wire, wherein the traction pulley is disposed at a position at which the resultant force of the tensions in the wire acting on the rotational shaft brings about a moment for causing the second swing member to swing.

According to this aspect, when a traction force is applied to the other end of the wire, the traction force is transferred, via the traction pulley around which the wire is looped, to the second swing member, which supports the traction pulley, and, of the traction force, a component in a tangential direction of the second swing member around the second swing shaft acts as a moment for causing the second swing member to swing, thereby causing the second swing member to swing about the second swing shaft with respect to the first swing member.

In this case, when a traction force is applied to the proximal end of the wire, the distal end of which is fixed, tensions in substantially the same direction are generated in the wire on both sides of the traction pulley with the rotational shaft therebetween, and the resultant force of the two tensions acts on the traction pulley. Specifically, the traction force applied to the proximal end of the wire is amplified to roughly double the number of turns between the traction pulley and the fixed pulley and acts on the traction pulley and the second swing member. Accordingly, the second swing member can be made to swing with a small force. Because the swing angle of the second swing member with respect to the first swing member is not structurally limited, it is possible to ensure a large swing angle of the second swing member with respect to the base member.

In this case, because the fixed pulley is provided on the first swing shaft so as to be rotatable, compared with a case in which the fixed pulley is provided between the second swing shaft and a joint that causes the first swing member to swing with respect to the base member, it is possible to reduce the length of a rigid part disposed closer to the distal end than the joint is and to improve the operability in a narrow place.

In the above-described aspect, the first swing shaft and the second swing shaft may be in parallel.

By doing so, a route of the wire can be roughly disposed in the same plane, thus making it possible to facilitate a reduction in diameter from the joint part to the distal end portion.

In the above-described aspect, the first swing shaft and the second swing shaft may be disposed on a skew line By doing so, because swinging of the first swing member about the first swing shaft with respect to the base member and swinging of the second swing member about the second swing shaft with respect to the first swing member are not performed in the same plane, the two swinging actions do not become redundant, thus making it possible to ensure a large range of motion.

In the above-described aspect, the rotational shaft of the traction pulley may further comprise a first slit that is provided in the first swing member and extending in the direction of the gap between the traction pulley and the fixed pulley, and a second slit that is provided in the second swing member and extending in a direction intersecting the first slit. The rotational shaft of the traction pulley may be disposed so as to move in a first slit and a second slit in the longitudinal directions of the first slit and the second slit.

By doing so, when the rotational shaft of the traction pulley is moved in the first slit in the direction of the gap between the traction pulley and the fixed pulley, the rotational shaft is also moved in the second slit, which intersects the first slit, thus forming a cam mechanism, and the second swing member, in which the second slit is provided, is made to swing about the second swing shaft with respect to the first swing member, in which the first slit is provided. By adjusting the positions of the first slit and the second slit and the relative angle therebetween, a moment can be amplified by means of the cam mechanism when the second swing member is made to swing in one direction with respect to the first swing member.

According to another aspect, the present invention provides a gripping tool including one of the above-described swing mechanisms, wherein the first swing member and the second swing member constitute a pair of gripping parts that are opened and closed by causing the first swing member to swing with respect to the second swing member.

According to this aspect, when a traction force is applied to the other end of the wire, the force for pulling the traction pulley is amplified by the wire, which is looped around the traction pulley and the fixed pulley, and the second swing member is made to swing with respect to the first swing member. Because the first swing member and the second swing member constitute a pair of gripping parts that mutually open and close, it is possible to close the pair of swinging parts with a small traction force and to grip a gripping target with a strong force.

REFERENCE SIGNS LIST 1 gripping tool
2 body part (base member)
3 swing mechanism
5 first gripping piece (first swing member)
6 second gripping piece (second swing member)
7, 20, 21, 22 traction pulley
8, 13, 19, 23 fixed pulley
9 wire
11 first slit
12 second slit
16 base member
15, 17 first swing member
18 second swing member
A first swing shaft
B second swing shaft
C, C1, C2 rotational shaft

The invention claimed is:
1. A swing mechanism comprising:
a base member;
a first swing member supported so as to swing about a first swing shaft with respect to the base member;
a second swing member connected to the first swing member, the second swing member being supported on the first swing member so as to swing about a second swing shaft, the second swing shaft being offset from the first swing shaft in a direction perpendicular to the first swing shaft;
a traction pulley supported on the second swing member so as to rotate about a rotational shaft offset in a direction perpendicular to the second swing shaft;
a fixed pulley supported so as to rotate about the first swing shaft; and
a wire having one end and another end, the wire being looped around the fixed pulley and the traction pulley, the one end of the wire being fixed to one of the base member, the first swing member, or the second swing member, and tensions in the wire having substantially the same magnitudes are generated on both sides of the traction pulley with the rotational shaft therebetween, by a traction force applied to the other end of the wire,
wherein the traction pulley is disposed at a position at which a resultant force of the tensions in the wire acting on the rotational shaft brings about a moment for causing the second swing member to swing.

2. A swing mechanism according to claim 1, wherein the first swing shaft and the second swing shaft are in parallel to each other.

3. A swing mechanism according to claim 1, wherein the first swing shaft and the second swing shaft are disposed on a skew line.

4. A swing mechanism according to claim 1, further comprising:
- a first slit provided in the first swing member, the first slit extending in the direction perpendicular to the second swing shaft, and
- a second slit provided in the second swing member, the second slit extending in a direction intersecting the first slit, wherein
- the rotational shaft of the traction pulley is disposed so as to move in the first slit and in the second slit in the longitudinal directions of the first slit and of the second slit.

5. A gripping tool comprising a swing mechanism according to claim 1, wherein the first swing member and the second swing member constitute a pair of gripping parts that are opened and closed by causing the first swing member to swing with respect to the second swing member.

* * * * *